(12) United States Patent  
Huang et al.

(10) Patent No.: US 7,999,004 B2  
(45) Date of Patent: Aug. 16, 2011

(54) COMPOUNDS HAVING ESTROGENIC ACTIVITY

(75) Inventors: Ching-jing Huang, Taipei (TW); Wei-Yi Cheng, Taipei (TW); Yueh-Hsiung Kuo, Taipei (TW); Yi-Ming Chiang, Taipei (TW)

(73) Assignee: National Taiwan University, Taipei (TW)

( * ) Notice: Subject to any disclaimer, the term of this patent is extended or adjusted under 35 U.S.C. 154(b) by 1097 days.

(21) Appl. No.: 11/673,433

(22) Filed: Feb. 9, 2007

(65) Prior Publication Data

US 2008/0193432 A1    Aug. 14, 2008

(51) Int. Cl.
*C07D 311/00* (2006.01)
*A61K 31/355* (2006.01)
(52) U.S. Cl. .................. 514/458; 549/407; 549/408
(58) Field of Classification Search .................. 514/458; 549/407, 408
See application file for complete search history.

(56) References Cited

OTHER PUBLICATIONS

Cohen et al , Total synthesis of All Eight Stereoisomers of alpah-tocopheryl Acetate.1981, Helvetica chimica Acta, vol. 64, Fasc. 4 nr.109, p. 1158-1173.*

Migliavacca et al , Theoretical Parameters to Characterize Antioxidants, 1997, Helvetica Chimica Acta, vol. 80 , 5, p. 1613-1626.*

Watanabe et al , Syntheses and Activities of Bioquinone Substances. II. Ubichromenol Phosphates and Related Compounds,1971, Chemical & Pharmaceutical Bulletin, 19(8), p. 1519-1525.*

* cited by examiner

*Primary Examiner* — Taylor Victor Oh
(74) *Attorney, Agent, or Firm* — WPAT, P.C.; Anthony King

(57) ABSTRACT

The present invention provides compounds having estrogenic activity selected from the group consisting of RRR-α-tocopherol, hydro-$Q_9$ chromene, coenzyme $Q_9$, cycloartane, 1-Feruloyl glycerol, γ-tocopherol-9, and analogues thereof. The compounds of the present invention activate ERα and ERβ, and express high estrogenic activity.

4 Claims, 7 Drawing Sheets

(A) ERα

(B) ERβ

(A) ERα

(B) ERβ

COMPOUNDS HAVING ESTROGENIC ACTIVITY

BACKGROUND OF THE INVENTION

1. Field of the Invention

The present invention provides compounds having estrogenic activity. More specifically, the compounds of the present invention are isolated from plants.

2. The Prior Arts

Through the period of menopause, menopausal women may suffer from symptoms like hot flashes, night sweats, and palpitation, etc. To relieve these symptoms, the menopausal women are usually recommended to be treated by hormone replacement therapy (HRT). However, previous studies indicate that administering estrogen alone for therapy may increase the risk of endometrial cancer. To minimize this deleterious effect caused by HRT, the co-administration of estrogens (e.g. 0.625 mg/day conjugated equine estrogens, CEE) along with progestin (e.g. 2.5 mg/day medroxyprogesterone acetate, MPA) is employed so as to reduce the increasing risk of endometrial cancer. On the other hand, in July 2002, the Women's Health Initiative (WHI) of USA reported that the continuous treatment by HRT for more than five years would lead to a higher risk of breast cancer, heart attacks, strokes, and pulmonary embolism. However, the therapy did reduce the women's risk of developing hip fractures and colorectal cancer.

Further, to compensate for losing the ability to secrete estrogen, providing menopausal women with estrogen is highly desirable for the prevention of menopausal symptoms and for the increase of risk of heart attacks and osteoporosis.

Conventional molecular biological studies have indicated that estrogen exerts its effect by binding to estrogen receptors and activate the expression of genes modulated by the estrogen, wherein the promoter of these genes comprising a sequence of estrogen responsive element (ERE). A compound that binds to an estrogen receptor and produces only partial effects is called a partial agonist, such as diethylstilbestrol (DES). A compound that binds to an estrogen receptor and does not produce any effect is called an antagonist or an anti-estrogen, such as tamoxifen, utilizing for inhibiting estrogen-dependent cancers. To date, two estrogen receptors, ERα and ERβ, have been identified. The distributions of these two receptors varied in different tissues. Accordingly, future investigation for treating the menopausal women might focus on a class of molecules called selective estrogen receptor modulators (SERM), which could stimulate estrogen receptors in the cells of blood vessels and bone tissues while bypassing other estrogen receptors in the cells of breast and ovarian, and benefit the numerous menopausal women.

Owing to the foregoing drawbacks exerted by conventional estrogens (e.g. CEE) isolated from animals, it is advantageous to develop a novel compound as a substitute thereof.

SUMMARY OF THE INVENTION

To solve the problems described above, an objective of the present invention is to provide compounds having estrogenic activity.

To accomplish the objective, the compound of the present invention is selected from the group consisting of RRR-α-tocopherol, hydro-$Q_9$ chromene, coenzyme Q9, cycloartane, 1-feruloyl glycerol, γ-tocopherol-9, and analogues thereof.

According to the present invention, a compound having estrogenic activity can be synthesized by known organic chemical synthesis or extracted and purified from the plants, such as but not limited to yam (Dioscorea).

According to the present invention, a compound activating ERα and/or ERβ, and expressing a high estrogenic activity is provided.

The present invention also provides a composition for improving symptoms caused by estrogen deficiency. The composition comprises an effective dose of the compound of the present invention, and a pharmaceutically acceptable carrier may further be included.

The present invention further provides a method for improving symptoms caused by estrogen deficiency. The method comprises administering an effective dose of the compound of the present invention. The estrogen deficiency symptoms include, but are not limit to, dry and aging skin, urinary incontinence, macular degeneration, hot flashes, night sweats, insomnia, and osteoporosis.

Although the present invention has been described below with reference to the preferred embodiment thereof, it is apparent to those skilled in the art that a variety of modifications and changes may be made without departing from the scope of the present invention which is intended to be defined by the appended claims.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

Figure 1:
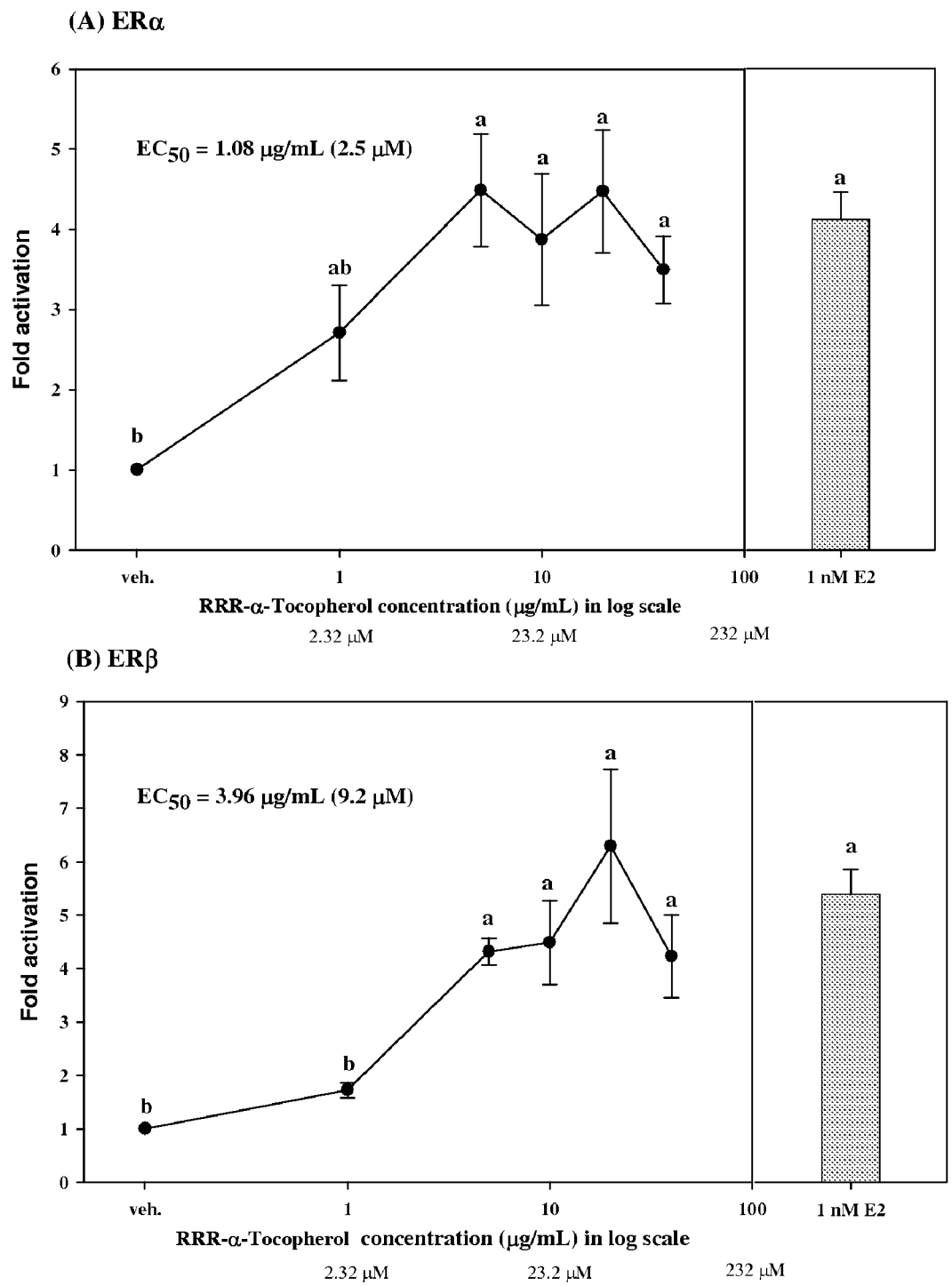
FIG. 1 shows a dose response curve of (A) GAL4-hERα; and (B) GAL4-hERβ of a compound 1.

According to the present invention, a compound having estrogenic activity is selected from the group consisting of RRR-α-tocopherol, hydro-$Q_9$ chromene, coenzyme $Q_9$, cycloartane, 1-feruloyl glycerol, γ-tocopherol-9, and analogues thereof.

The RRR-α-tocopherol of the present invention is represented by the structural formula (1):

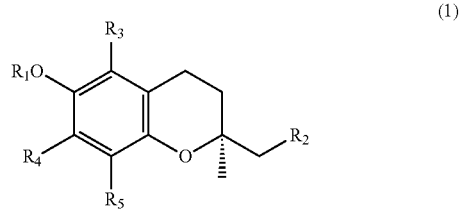

wherein $R_1$ is hydrogen, acetyl group (Ac, $CH_3COO-$), an alkyl group having 1 to 6 carbon atoms, or as the below structural formula (1-1) or (1-2)

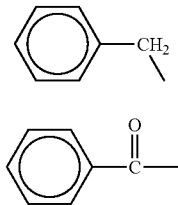
(1-1)

(1-2)

wherein $R_2$ is as the below structural formula (1-3), (1-4), or (1-5)

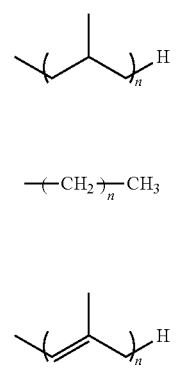
(1-3)

(1-4)

(1-5)

wherein n is from 0 to 6; and $R_3$, $R_4$, $R_5$ is hydrogen or methyl independently.

The hydro-$Q_9$ chromene of the present invention is represented by the structural formula (2):

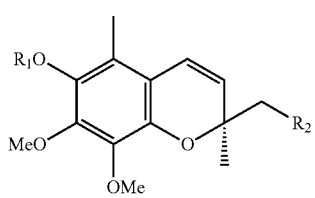
(2)

wherein $R_1$ is hydrogen, acetyl group, an alkyl group having 1 to 6 carbon atoms, or as the below structural formula (2-1) or (2-2)

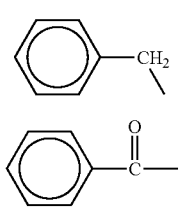
(2-1)

(2-2)

wherein $R_2$ is as the below structural formula (2-3), (2-4), or (2-5)

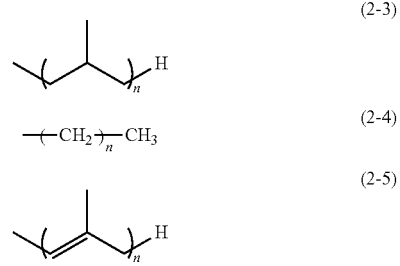
(2-3)

(2-4)

(2-5)

wherein n is from 0 to 6; and Me is methyl.

The coenzyme $Q_9$ of the present invention is represented by the structural formula (3):

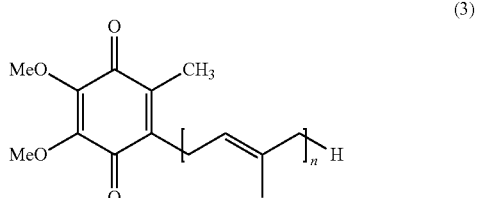
(3)

wherein Me is methyl, and n is from 0 to 9.

The cycloartane of the present invention is represented by the structural formula (4):

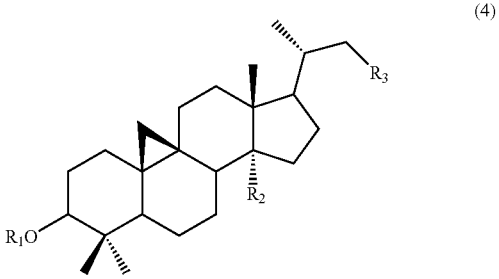
(4)

wherein $R_1$ is hydrogen, acetyl group, an alkyl group having 1 to 6 carbon atoms, or as the below structural formula (4-1) or (4-2)

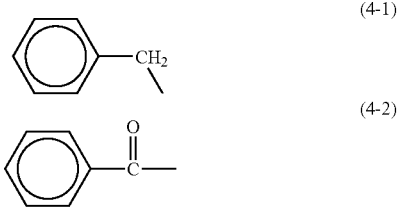
(4-1)

(4-2)

wherein $R_2$ is hydrogen, methyl alkyl, or carboxyl; and $R_3$ is as the below structural formula (4-3), (4-4), (4-5), (4-6), (4-7), (4-8), (4-9), (4-10), (4-11), or (4-12):

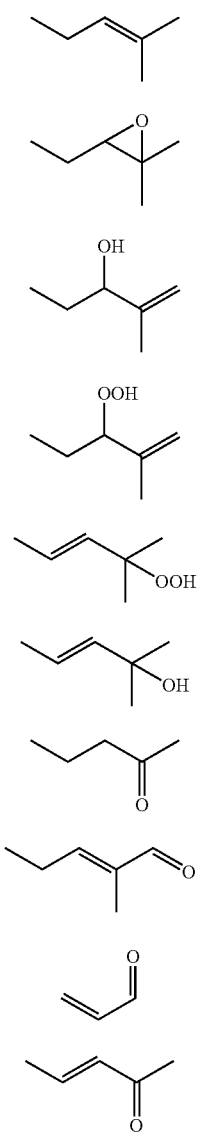

(4-3)
(4-4)
(4-5)
(4-6)
(4-7)
(4-8)
(4-9)
(4-10)
(4-11)
(4-12)

The 1-feruloyl glycerol of the present invention is represented by the structural formula (5-1):

(5-1)

wherein $R_1$ is hydrogen, acetyl group, an alkyl group having 1 to 6 carbon atoms, or as the below structural formula (5-1-1) or (5-1-2)

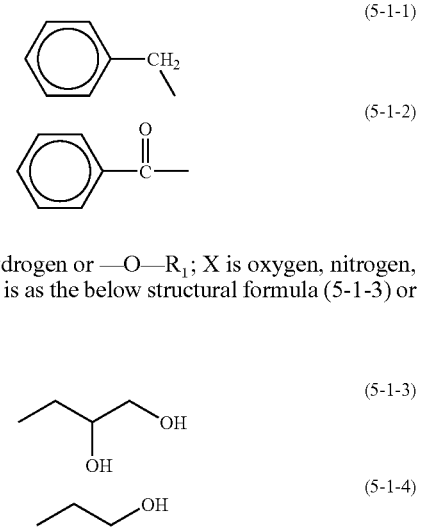

(5-1-1)
(5-1-2)

wherein $R_2$ is hydrogen or —O—$R_1$; X is oxygen, nitrogen, or sulfur; and $R_3$ is as the below structural formula (5-1-3) or (5-1-4):

(5-1-3)
(5-1-4)

and the 1-feruloyl glycerol of the present invention is also represented by the structural formula (5-2):

(5-2)

wherein $R_1$ is hydrogen, acetyl group, an alkyl group having 1 to 6 carbon atoms, or as the below structural formula (5-2-1) or (5-2-2)

(5-2-1)
(5-2-2)

wherein $R_2$ is hydrogen or —O—$R_1$, and X is oxygen, nitrogen, or sulfur.

The γ-tocopherol-9 of the present invention is represented by the structural formula (6):

(6)

wherein $R_1, R_2, R_3$ are independently hydrogen, acetyl group, an alkyl group having 1 to 6 carbon atoms or as the structural formula (6-1) or (6-2)

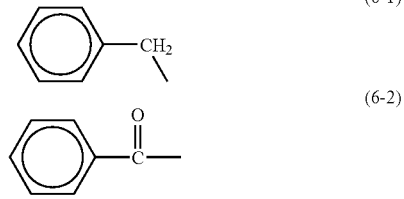

wherein n is from 0 to 9.

In accordance to the present invention, the compound having estrogenic activity can effectively activate ERα and ERβ, and exhibit a high estrogenic activity. Hence, the compound of the present invention can be used as a substitute or an adjuvant supplement of the animal estrogen. Moreover, it is apparent to those skilled in the art that the appropriate supplement with the compound in accordance with the present invention is useful to improve the symptoms caused by estrogen deficiency including but not limited to dry and aging skin, urinary incontinence, macular degeneration, hot flashes, night sweats, insomnia, and osteoporosis.

Embodiment 1

Establishment of Transactivation Assay for Estrogen Activity Testing

To evaluate the estrogen activity, the pBKCMV plasmid containing the gene of GAL4hERα (or β) LBD chimeric receptors was co-transfected with a plasmid containing the $(UAS)_4$-alkaline phosphatase reporter gene into CHO-K1 cells. When a test sample was reacted with ER, the GAL4 was mediated to bind specifically with the UAS upstream of the reporter gene so as to activate the expression of the reporter gene, i.e. the alkaline phosphatase (ALP) enzyme. By measuring the alkaline phosphatase activity, we can detect the estrogen activity of the sample.

First, a CHO-K1 cell line (CCRC 60006), obtained from the Culture Collection and Research Center (CCRC) of the Food Industry Research and Development Institute (FIRDI), Hsinchu, Taiwan, R.O.C., was cultured in a Ham's F12 nutrient mixture (GIBCOBRL® 11765-054) medium supplemented with 10% fetal bovine serum (FBS). Cells were grown to confluence and seeded into 96-well microplates for a day. Before transfection, the two plasmids DNA in equal proportions were added to a mixture of the Fugene 6 transfection reagent and Ham's F12 medium, and then incubated for 20 min. At transfection, the fugene 6-DNA mixture was then added to the cells after the original FBS containing medium was removed.

After 5 h of incubation, the cells were added with Ham's F-12 medium containing 10% serum replacement and vehicle (ethanol or DMSO), 1 nM 17β-estradiol ($E_2$) or samples of appropriate concentrations. After a 2-day culture, an aliquot of the medium was taken for the analysis of alkaline phosphatase activity. The alkaline phosphatase activity was analyzed by using 4-Nitrophenyl phosphate disodium salt hexahydrate (pNPP) as a substrate, and then the absorbance at 405 nm was measured in a microplate reader. In every batch of the transactivation assay, a known ER activator (1 nM 17β estradiol, i.e. $E_2$) was included as the positive control, and vehicle-treated cells were used as the negative control.

To confirm the efficacy of the assay, 17β estradiol ($E_2$) and three isoflavones (e.g. genistein, daidzein, and geistein) were tested. It is observed that increases in the concentration of $E_2$ resulted in a dose-dependent manner in the ALP activity. And the $EC_{50}$ value of ERα and ERβ activation is $8.79 \times 10^{-6}$ nM and $2 \times 10^{-5}$ nM, respectively. The $EC_{50}$ value of ERα and ERβ activation by genistein (isoflavones) is 298.49 nM and 3.41 nM respectively; the $EC_{50}$ value of ERα and ERβ activation by daidzein is 874.86 nM and 52.4 nM respectively; and the $EC_{50}$ value of ERα and ERβ activation by geistein is 726.03 nM and 13.9 nM respectively. Hence, we observed the isoflavones exhibit higher activity to ERβ as expected.

Embodiment 2

The Fractions Having Estrogen Activity Extracted from Yam (Dioscorea)

18 kg of the powder from yam (Dioscorea) without blanching was added in batches (500 g of the powder each time) to 10-fold volume solvent (i.e. ethyl acetate). The mixture was then stirred with a stir bar at room temperature for 2 days. Subsequently, the mixture was filtered twice through vacuum filtration (a white porcelain funnel fitted with Whatman #2 Filter paper). The re-filtered filtrate was evaporated at 45-50° C. on a rotary evaporator to remove the solvent and then the ethyl acetate extract was obtained.

The yam (Dioscorea) ethyl acetate extract was dissolved in EA, and mixed with a 1.5-fold volume of coarse silica gel (230-400 mesh) for adsorption, and then loaded on a column packed with 15-fold volume of silica gel (70-230 mesh) for chromatography. The column was eluted with a mixture of n-hexane and ethyl acetate (EA). The column was successively eluted with 3.75 L of the 100% n-hexane, 3.5 L of the 2% EA/98% n-hexane, and 4.5 L of the 5% EA/95% n-hexane and the last 2 L of eluate were collected. The column was then eluted with 1.5 L of the 10% EA/90% n-hexane and the eluate was collected. The two eluates was pooled (total 3.5 L) and evaporated on a rotary evaporator and subjected to a second silica gel column chromatography. The second column chromatography was eluted with 0.5 L of the 100% n-hexane, and 0.375 L of the 1% EA/99% n-hexane and the last 0.25 L of eluate were collected.

The fraction obtained from the second open column silica gel chromatography of yam (Dioscorea) EA extract was further separated by a preparative HPLC. The HPLC was performed on a Phenomenex Luna column (silica 10 mm×250 mm; 5 μm) with the RID-10A Shimadzu refractive index detector, and 10% EA/90% n-hexane was used as a mobile phase with a flow rate of 3 ml/min. The fraction eluted at a period between 6 min 40 sec to 7 min 40 sec was further separated by a second HPLC. In the second HPLC, the mobile phase was a mixture of 2% EA, 1% methanol, 87% n-hexane, and 10% chloroform ($CHCl_3$) and the flow rate was 2 ml/min. The fraction eluted at a period between 11 min to 11 min 30 sec was collected and further analyzed by NMR. The chemical structure was identified as RRR-α-tocopherol (compound 1). The RRR-α-tocopherol, with a molecular weight of 430.38 Dalton, has a molecular formula of $C_{29}H_{50}O_2$ and a structural formula (7) shown as below:

(7)

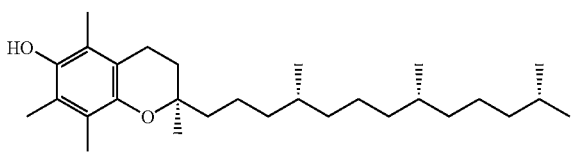

The compound 1 was dissolved in absolute alcohol to test the ER activity by the transactivation assay of embodiment 1, and the result was shown in FIG. 1.

As shown in FIG. 1, it is observed that an increase in the concentration of compound 1 resulted in a dose-dependent increase in the ALP activity. When the concentration of compound 1 is 5 μg/mL (11.6 μM), the maximal activation of ERα is achieved. And when the concentration of compound 1 is 20 μg/mL (46.5 μM), the maximal activation of ERβ is achieved. The $EC_{50}$ value for ERα is 1.08 μg/mL (2.5 μM), and the $EC_{50}$ value for ERβ is 3.96 μg/mL (9.2 μM).

Embodiment 3

The yam (Dioscorea) EA extract obtained from embodiment 2 was further fractionated by silica gel column chromatography. The column was successively eluted with 3.75 L of the 100% n-hexane, 3.5 L of the 2% EA/98% n-hexane, and 4.5 L of the 5% EA/95% n-hexane and the last 2 L of eluate was collected. The column was then eluted with 1.5 L of the 10% EA/90% n-hexane and the eluate was collected. The two eluates was pooled (total 3.5 L) and evaporated on a rotary evaporator and subjected to a second silica gel column chromatography. The second column chromatography was eluted with 0.5 L of the 100% n-hexane, and 0.375 L of the 1% EA/99% n-hexane and 0.25 L of the 2% ethyl acetate/98% n-hexane and the last 0.25 L of eluate was collected. The fraction obtained from the second open column silica gel chromatography of yam (Dioscorea) EA extract was further separated by a preparative HPLC. The mobile phase was 10% EA/90% n-hexane with a flow rate of 3 ml/min. The fraction eluted at a period between 6 min 30 sec to 8 min 20 sec was further separated by a third silica gel column chromatography. The third column chromatography was eluted with 0.2 L 1.5% EA/98.5% n-hexane and the eluate was collected and separated by a second HPLC. In the second HPLC, the mobile phase was 10% EA/90% n-hexane and the flow rate was 3 ml/min. The fraction eluted at a period between 7 min 3 sec to 7 min 34 sec was collected and further analyzed by NMR. The chemical structure was identified as hydro-$Q_9$ chromene (compound 2), a derivative of coenzyme $Q_9$. The hydro-$Q_9$ chromene, with a molecular weight of 794.62 Dalton, has a molecular formula of $C_{54}H_{82}O_4$ and a structural formula (8) shown as below:

(8)

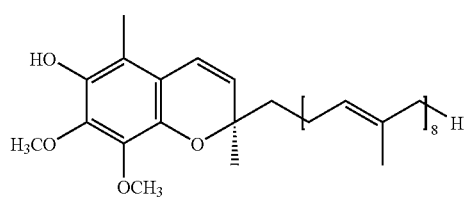

Figure 2:
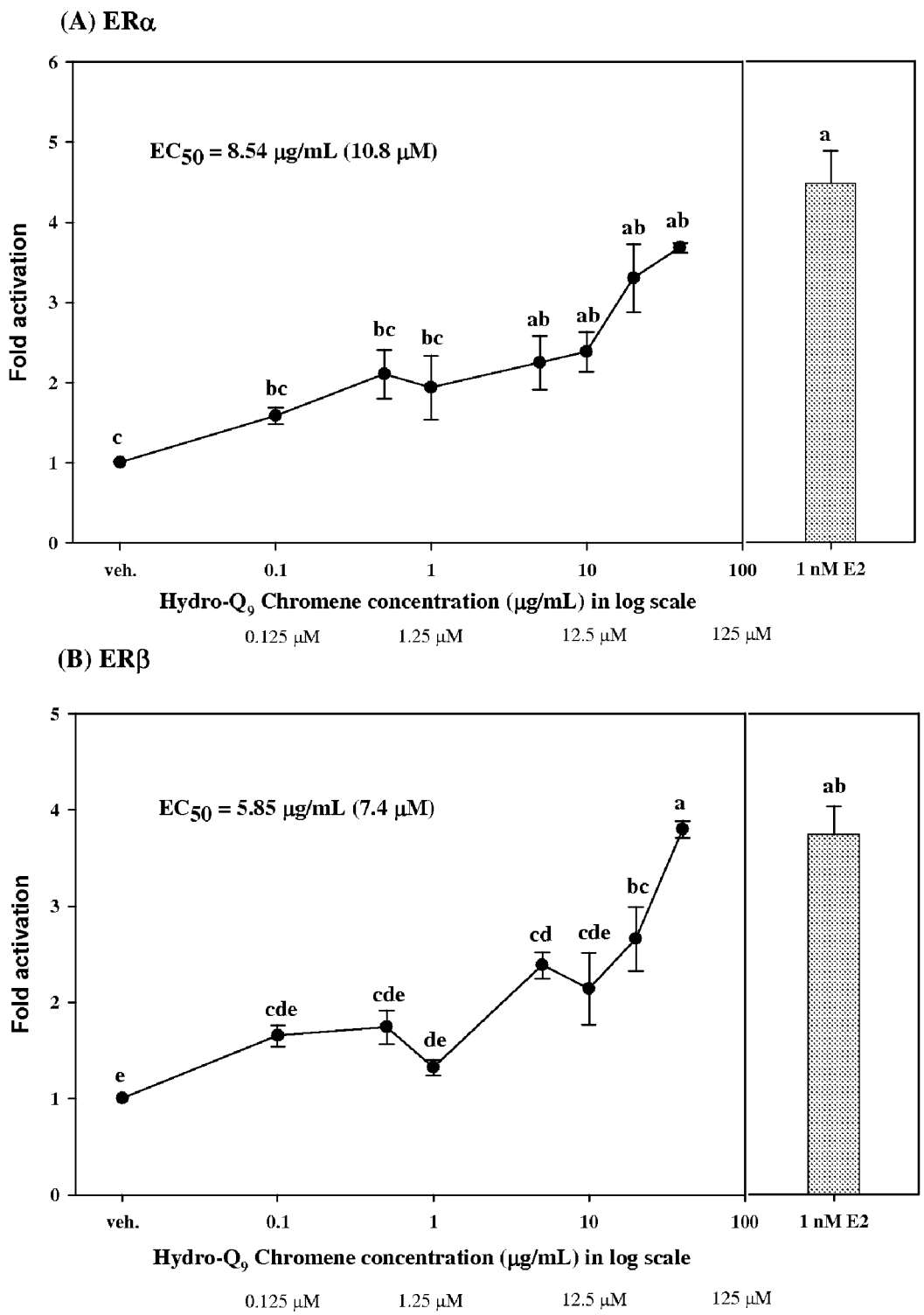
FIG. 2 shows a dose response curve of (A) GAL4-hERα; and (B) GAL4-hERβ of compound 2.

The compound 2 was dissolved in absolute alcohol to test the ER activity by the transactivation assay of embodiment 1, and the result was shown in FIG. 2.

As shown in FIG. 2, it is observed that an increase in the concentration of compound 2 resulted in a dose-dependent increase in the ALP activity. When the concentration of compound 2 is 40 μg/mL (50.34 μM), the maximal activation of ERα and ERβ is achieved to 3.68-fold activation and 3.79-fold activation respectively. The $EC_{50}$ value for ERα is 8.54 μg/mL (10.8 μM), and the $EC_{50}$ value for ERβ is 5.85 μg/mL (7.4 μM).

Embodiment 4

The yam (Dioscorea) EA extract obtained from embodiment 2 was further fractionated by silica gel column chromatography. The column was successively eluted with 3.75 L of the 100% n-hexane, 3.5 L of the 2% EA/98% n-hexane, 4.5 L of the 5% EA/95% n-hexane, and 2 L of the 10% EA/90% n-hexane and the last 500 mL of the eluate was collected. The eluate was then evaporated on a rotary evaporator and separated by a preparative HPLC. The mobile phase was a mixture of 2% ethyl acetate, 1% methanol, 87% n-hexane, and 10% chloroform ($CHCl_3$) and the flow rate was 2 ml/min. The fraction eluted at a period between 8 min 30 sec to 9 min 20 sec was collected and further analyzed by NMR. The chemical structure was identified as coenzyme $Q_9$ (compound 3). The coenzyme $Q_9$ with a molecular weight of 794.62 Dalton, has a molecular formula of $C_{54}H_{82}O_4$, and a structural formula (9) thereof is as below:

(9)

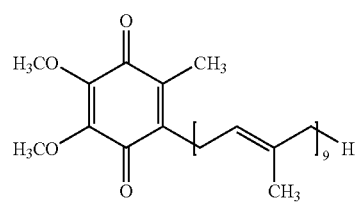

Figure 3:
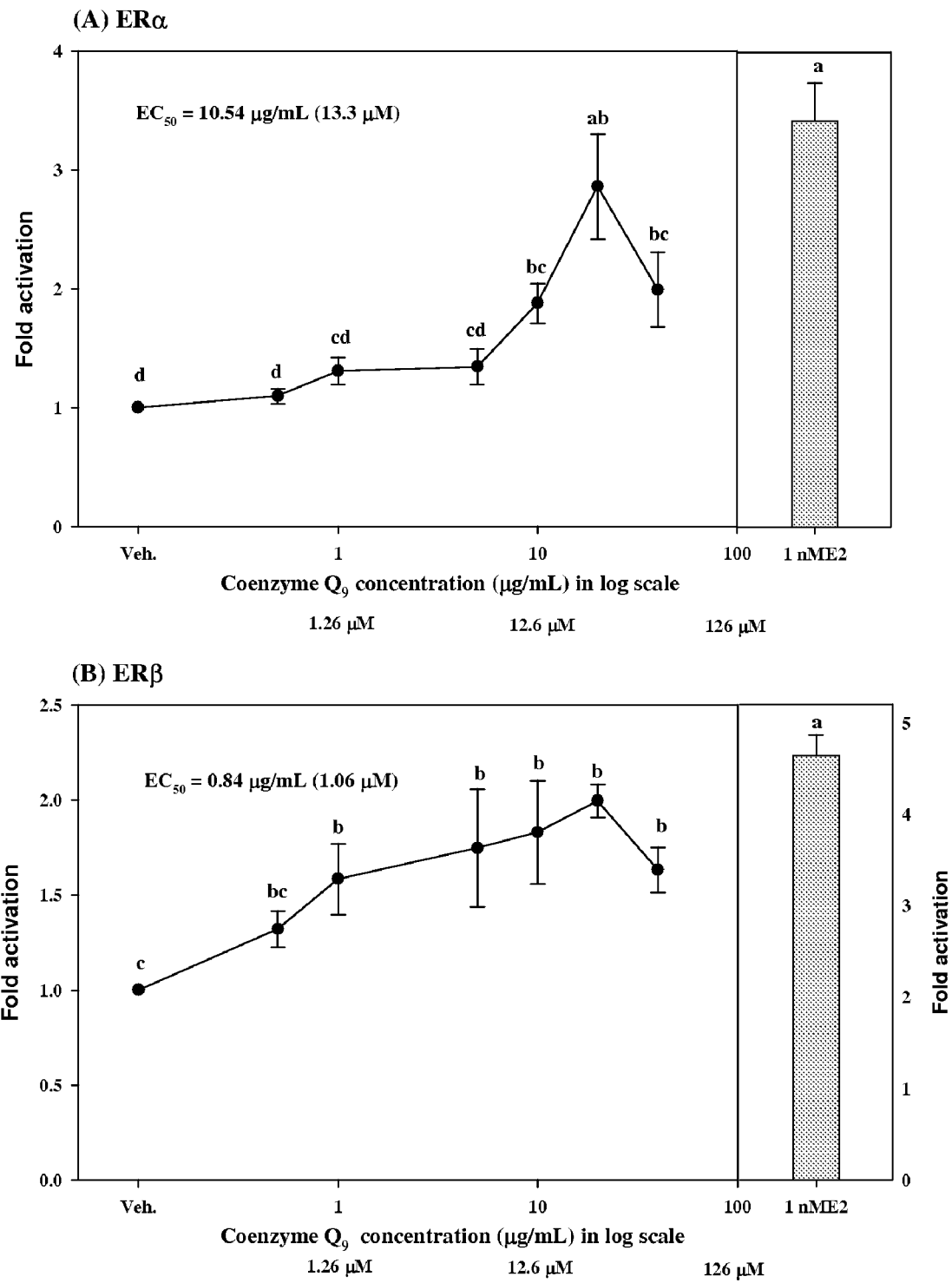
FIG. 3 shows a dose response curve of (A) GAL4-hERα; and (B) GAL4-hERβ of a compound 3.

The compound 3 was dissolved in absolute alcohol to test the ER activity by the transactivation assay of embodiment 1, and the result was shown in FIG. 3.

As shown in FIG. 3, it is observed that an increase in the concentration of compound 3 resulted in a dose-dependent increase in the ALP activity. When the concentration of compound 3 is 20 μg/mL (25.2 μM), the maximal activation of ERα and ERβ is achieved. The $EC_{50}$ value for ERα is 40.54 μg/mL (13.3 μM), and the $EC_{50}$ value for ERβ is 0.84 μg/mL (1.06 μM).

Embodiment 5

The yam (Dioscorea) EA extract obtained from embodiment 2 was further fractionated by silica gel column chromatography. The column was successively eluted with 3.75 L of the 100% n-hexane, 3.5 L of the 2% EA/98% n-hexane, 4.5 L of the 5% EA/95% n-hexane, and 3 L of the 10% EA/90% n-hexane and the last 500 mL of the eluate was collected. The eluate was then evaporated on a rotary evaporator and separated by a preparative HPLC. The mobile phase was 10% EA/90% n-hexane and the flow rate was 4.5 ml/min. The fraction eluted at a period between 8 min 14 sec to 9 min 10 sec was collected and further analyzed by NMR. The chemical structure was identified as cycloartane (compound 4). The cycloartane with a molecular weight of 426.72 Dalton, has a molecular formula of $C_{30}H_{50}O$, and a structural formula (10) thereof is as below:

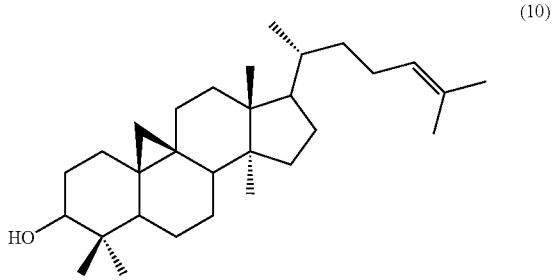

(10)

Figure 4:
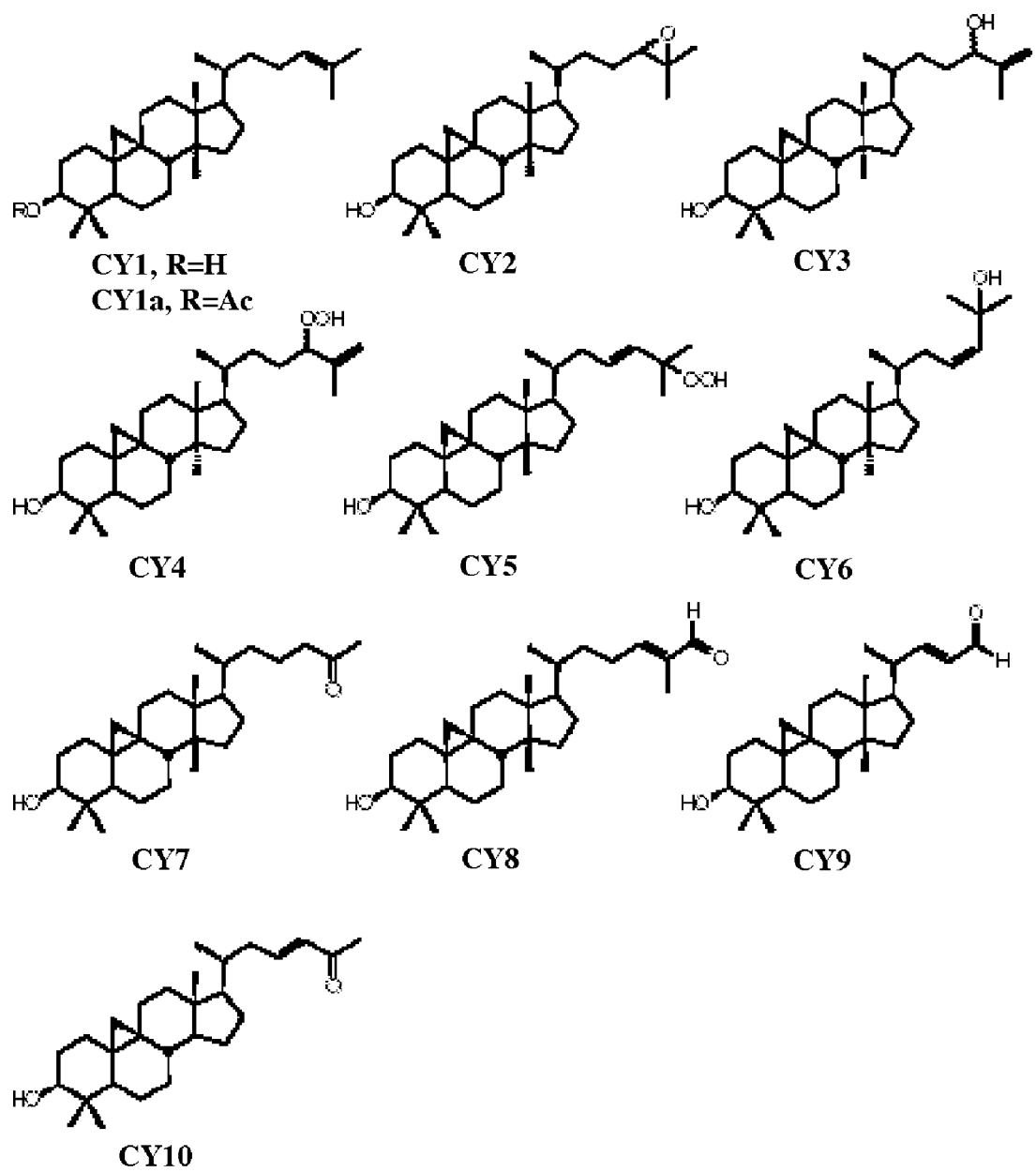
FIG. 4 shows chemical structures and abbreviations of series compounds of cycloartane.

The chemical structures and abbreviations of the series compounds of cycloartane are shown in FIG. 4. These compounds were dissolved in absolute alcohol to test the ER activity by the transactivation assay of embodiment 1, and the result was shown in FIG. 5.

Figure 5:
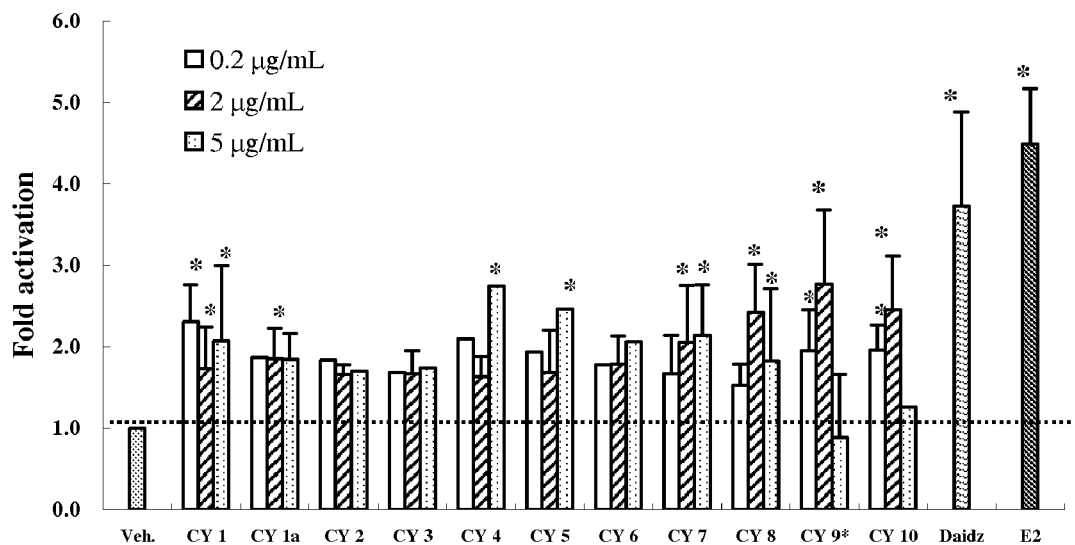
FIG. 5 shows the activation of (A) GAL4-hERα; and (B) GAL4-hERβ by series compounds of cycloartane.
Figure 5:
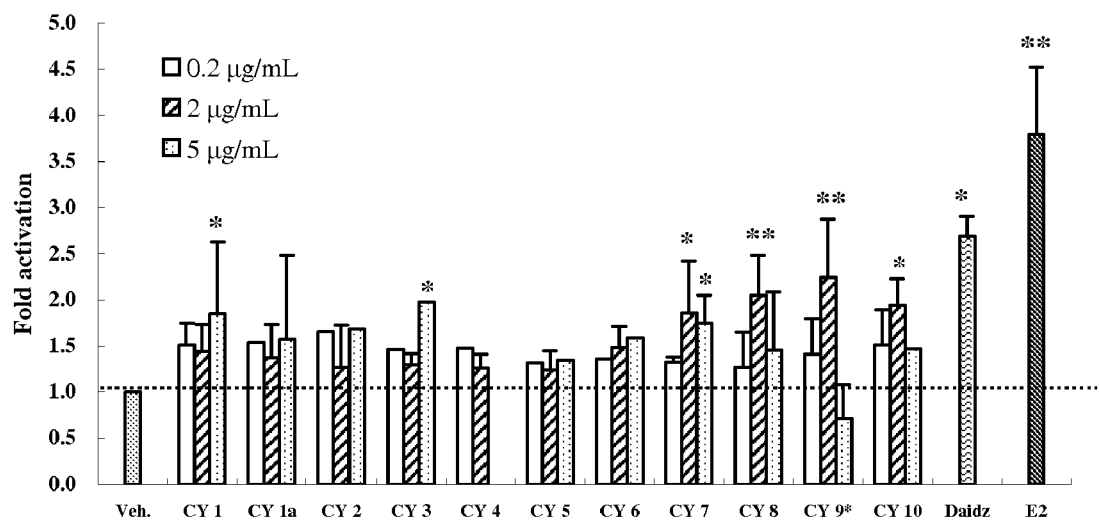

As shown in FIG. 5, at a concentration of 2 μg/mL, compounds CY1, CY1a, CY7, CY8, CY9, and CY10 led to significantly higher ALP activity than the vehicle control through the activation ERα. Among those, CY9 shows the highest activation of 2.25-fold, which is 73.8% and 44.5% respectively of the activation of 2 μM daidzein and 1 nM $E_2$. In regard to ERβ, at a concentration of 2 μg/mL, compounds CY1, CY1a, CY7, CY8, CY9, and CY10 led to significantly higher ALP activity than the vehicle control. Among those, CY9 shows the highest activation of 2.78-fold, which is 65% and 51% respectively of the activation of 2 μM daidzein and 1 nM $E_2$.

Embodiment 6

The yam (Dioscorea) EA extract obtained from embodiment 2 was further fractionated by silica gel column chromatography. The column was successively eluted with 3.75 L of the 100% n-hexane, 3.5 L of the 2% EA/98% n-hexane, 4.5 L of the 5% EA/95% n-hexane, 9 L of the 10% EA/90% n-hexane, 4 L of the 20% EA/80% n-hexane, 3.5 L of the 30% EA/70% n-hexane, and 4 L of the 50% EA/50% n-hexane and the last 1.5 L of the eluate was collected. The eluate was evaporated on a rotary evaporator and subjected to a second silica gel column chromatography. The eluate (200 mL) obtained by eluting the column with 100% chloroform was collected. The fraction obtained from the second open column silica gel chromatography of yam EA extract was further separated by a preparative HPLC. The mobile phase was a mixture of 2% ethyl acetate, 2% methanol, and 96% dichloromethane and the flow rate was 3 ml/min. The fraction eluted at a period between 10 min to 11 min 30 sec was collected and further analyzed by NMR. The chemical structure was identified as 1-feruloyl glycerol (compound 5). The 1-feruloyl glycerol with a molecular weight of 268.09 Dalton, has a molecular formula of $C_{13}H_{16}O_6$, and a structural formula (11) thereof is as below:

(11)

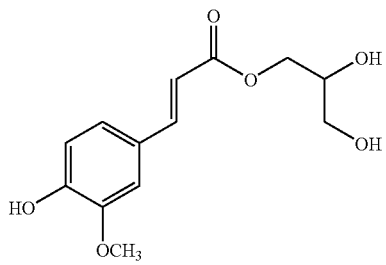

Figure 6:
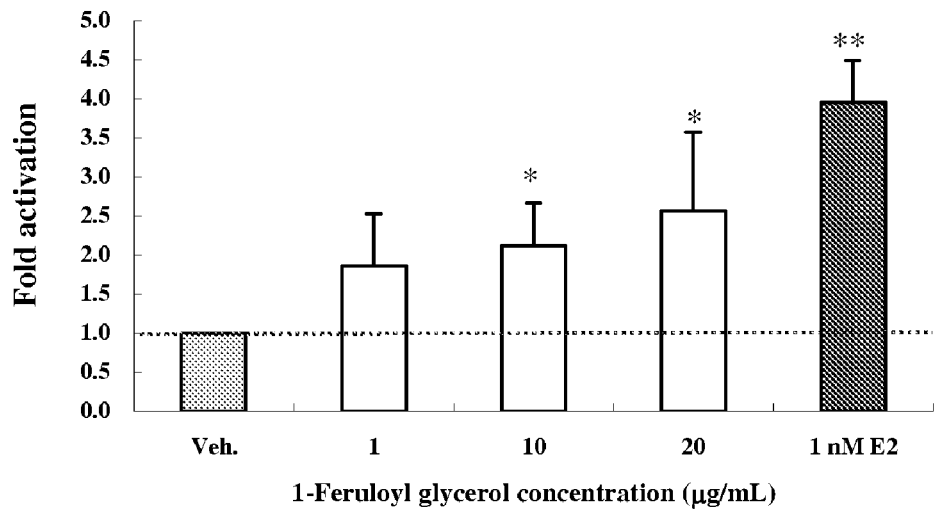
FIG. 6 shows the activation of (A) GAL4-hERα; and (B) GAL4-hERβ by a compound 5.
Figure 6:
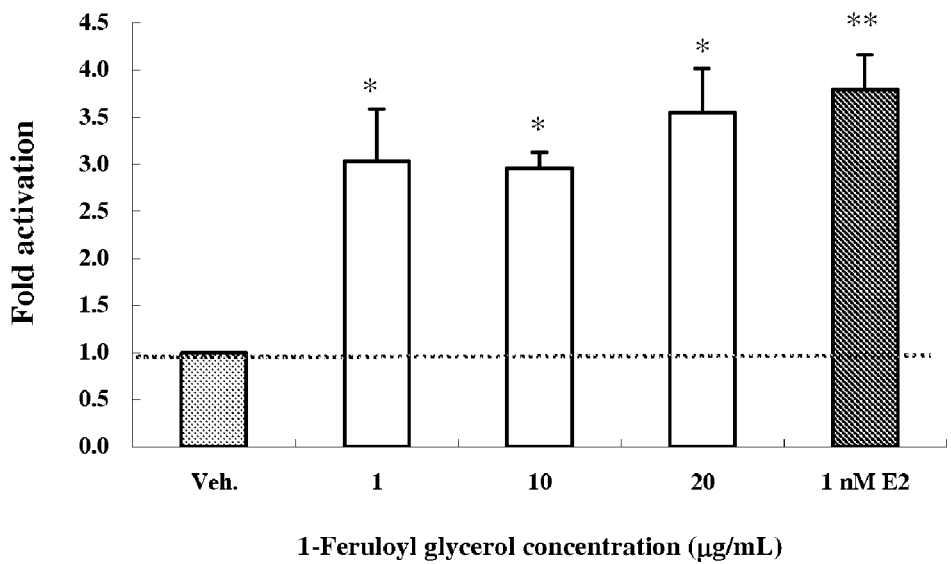

The fraction with compound 5 was dissolved with absolute alcohol to test the ER activity by the transactivation assay of embodiment 1, and the result was shown in FIG. 6.

As shown in FIG. 6, when transfected cells were treated with three concentrations of compound 5, significant increases in the ALP activity are observed.

Embodiment 7

The yam (Dioscorea) EA extract obtained from embodiment 2 was further fractionated by silica gel column chromatography. The column was successively eluted with 3.75 L of the 100% n-hexane, 3.5 L of the 2% EA/98% n-hexane, 4.5 L of the 5% EA/95% n-hexane, and 2 L of the 10% EA/90% n-hexane and the last 500 mL of the eluate was collected. The eluate was then evaporated on a rotary evaporator and separated by a preparative HPLC. The mobile phase was a mixture of 2% ethyl acetate, 1% methanol, 87% n-hexane, and 10% chloroform ($CHCl_3$) and the flow rate was 2 ml/min. The fraction eluted at a period between 12 min 36 sec to 14 min 39 sec was further purified by a second HPLC. The mobile phase was 12% ethyl acetate/88% n-hexane with a flow rate of 3 ml/min. The fraction eluted at a period between 8 min 26 sec to 9 min 32 sec was collected and further analyzed by NMR. The chemical structure was identified as γ-tocopherol-9 (compound 6). The γ-tocopherol-9 with a molecular weight of 750.63 Dalton, has a molecular formula of $C_{53}H_{82}O_2$, and a structural formula (12) thereof is as below:

(12)

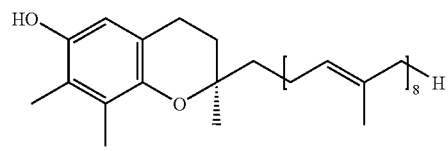

Figure 7:
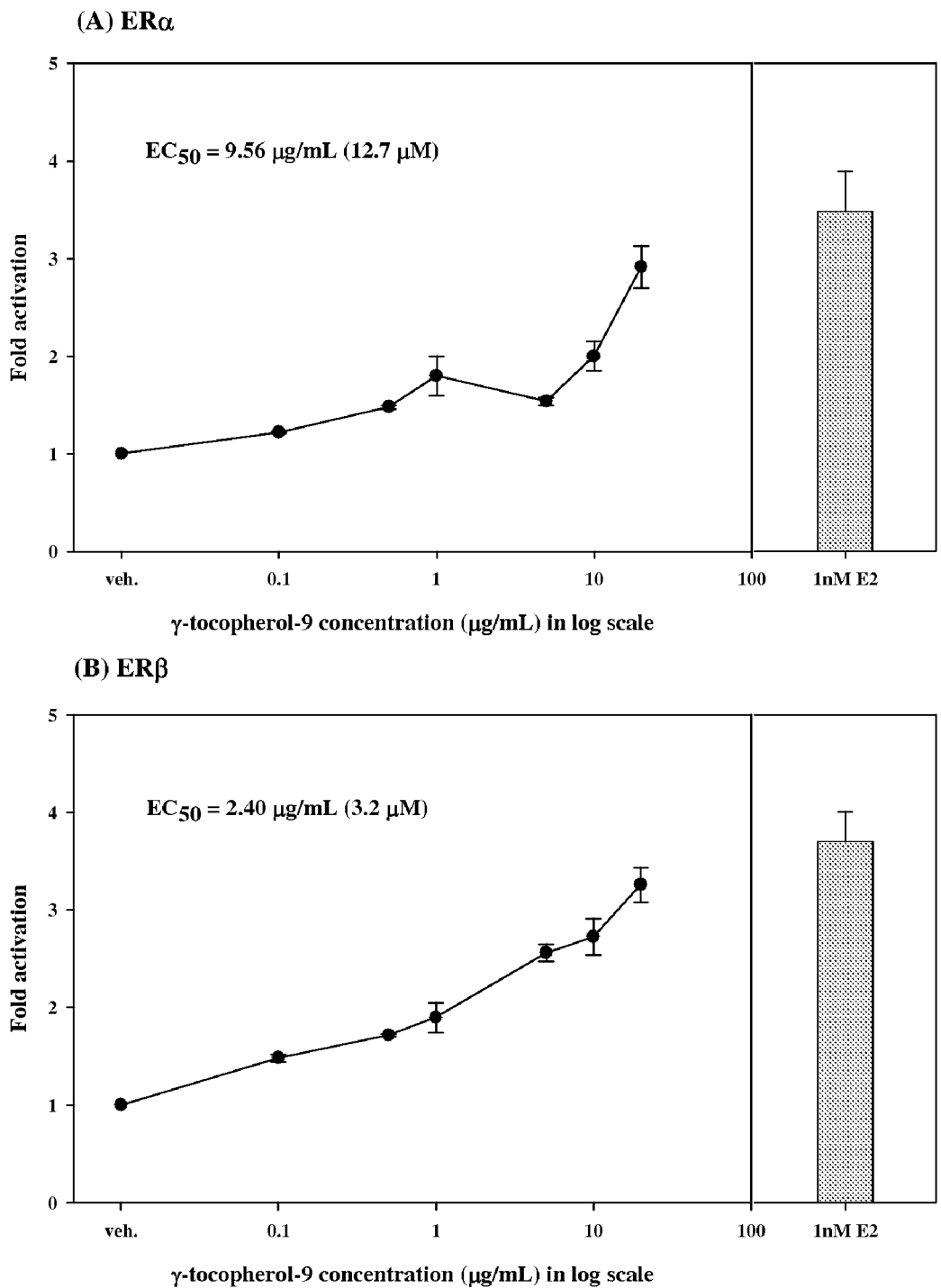
FIG. 7 shows a dose response curve of (A) GAL4-hERα; and (B) GAL4-hERβ of a compound 6.

The compound 6 was dissolved in absolute alcohol to test the ER activity by the transactivation assay of embodiment 1, and the result was shown in FIG. 7.

As shown in FIG. 7, it is observed that increases in the concentration of compound 6 resulted in a dose-dependent increase in the ALP activity. When the concentration of compound 6 is 20 μg/mL (26.64 μM), the maximal activation of the ERα and ERβ is achieved (2.91-fold activation and 3.26-fold activation, respectively). The $EC_{50}$ value for ERα is 9.56 μg/mL (12.7 μM), and the $EC_{50}$ value for ERβ is 2.40 μg/mL (3.2 μM).

What is claimed is:
1. A method for activating an estrogen receptor, comprising administering an effective dose of the compound as represented by the structural formula (8):

(8)

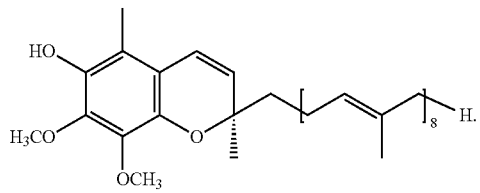

2. The method as claimed in claim 1, wherein the estrogen receptor is selected from the group consisting of ERα, ERβ and mixture thereof.

3. A method for activating an estrogen receptor, comprising administering an effective dose of RRR-α-tocopherol or γ-tocopherol-9.

4. The method as claimed in claim 3, wherein the estrogen receptor is selected from the group consisting of ERα, ERβ and mixture thereof.

\* \* \* \* \*

UNITED STATES PATENT AND TRADEMARK OFFICE
CERTIFICATE OF CORRECTION

PATENT NO.         : 7,999,004 B2                        Page 1 of 1
APPLICATION NO.    : 11/673433
DATED              : August 16, 2011
INVENTOR(S)        : Ching-jang/Cheng Huang et al.

It is certified that error appears in the above-identified patent and that said Letters Patent is hereby corrected as shown below:

Title Page, Item (75) Inventors;
First Inventor, delete "Ching-jing" and insert --Ching-jang--.

Signed and Sealed this
Sixth Day of December, 2011

David J. Kappos
*Director of the United States Patent and Trademark Office*